United States Patent [19]
Heider et al.

[11] Patent Number: 5,962,700
[45] Date of Patent: Oct. 5, 1999

[54] BUTYROLACTONE-PREPARATION PROCESS

[75] Inventors: Marc Heider, Neustadt; Thomas Rühl, Frankenthal; Jochem Henkelmann, Mannheim; Susanne Stutz, Weinheim; Thomas Preiss, Ludwigshafen; Heinz Rütter, Hochdorf-Assenheim; Martin Schäfer, Ludwigshafen; Arthur Höhn, Kirchheim, all of Germany

[73] Assignee: BASF Aktiengesellschaft, Ludwigshafen, Germany

[21] Appl. No.: 09/011,607

[22] PCT Filed: Aug. 6, 1996

[86] PCT No.: PCT/EP96/03472

§ 371 Date: Feb. 12, 1998

§ 102(e) Date: Feb. 12, 1998

[87] PCT Pub. No.: WO97/07111

PCT Pub. Date: Feb. 27, 1997

[30] Foreign Application Priority Data

Aug. 19, 1995 [DE] Germany ............................ 195 30 549
Nov. 29, 1995 [DE] Germany ............................ 195 44 408

[51] Int. Cl.⁶ .................................................. C07D 307/33
[52] U.S. Cl. ........................................... 549/295; 549/323
[58] Field of Search ...................... 549/295, 323

[56] References Cited

FOREIGN PATENT DOCUMENTS 63 68580  3/1988  Japan .

OTHER PUBLICATIONS

Chemical Abstracts, vol. 121, Aug. 29, 1994, No. 9.
Derwent JP 63068580, 1988.
Organometallics, 1991, 10, 2493–2498.
Inorganica Chimica Acta, 220 (1994), 45–53.
Industrielle Organische Chemie, Verlag Chemie, 1978.

*Primary Examiner*—Ba K. Trinh
*Attorney, Agent, or Firm*—Keil & Weinkauf

[57] ABSTRACT

A process for the preparation of butyrolactones of the formula I

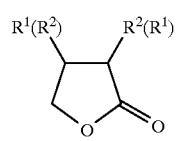

I where the substituents $R^1$ and $R^2$ are hydrogen, alkyl or hydroxyalkyl groups, or aryl and trialkylsilyl groups, if appropriate carrying inert: substituents, is described in which an alkyne of the formula II

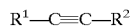

$$R^1-C\equiv C-R^2 \qquad II$$

where the substituents have the meanings indicated above, is reacted under reducing conditions at elevated pressure and elevated temperature with carbon monoxide CO and hydrogen in the presence of a transition metal catalyst or with carbon monoxide and water in the presence of a transition metal catalyst.

14 Claims, No Drawings

BUTYROLACTONE-PREPARATION PROCESS

This application is 371 of PCT/EP96/03472, dated Aug. 6, 1996.

The invention relates to a process for the preparation of butyrolactones by reaction of acetylenes with carbon monoxide and hydrogen gas or hydrogen formed in situ in the presence of transition metal catalysts via the stage of the corresponding 2-(5H)-furanones, and to an improved process for the preparation of these furanones, which can also be converted into the butyrolactones in a separate hydrogenation step.

γ-Butyrolactone is an important product of the chemical industry. It is used as an intermediate for the preparation of pyrrolidone and its derivatives and also as a solvent.

Butyrolactone is prepared industrially by various multistage processes. The dehydrocyclization of 1,4-butanediol thus leads in high yields to butyrolactone. Alternatively, maleic anhydride can be partially hydrogenated to give butyrolactone. Both starting compounds for the preparation of γ-butyrolactone are only accessible from basic chemicals in multistage processes (Weissermel, Arpe, Industrielle Organische Chemie [Industrial Organic Chemistry], 2nd Edition 1978, Verlag Chemie, p. 97).

The reaction of alkynes and CO in the presence of rhodium catalysts has been described for the preparation of unsaturated 2(5H)-furanones, which are used as intermediates for the preparation of drugs (Joh et al., Inorg. Chim. Acta, 220 (1994) 45; Organometallics 10 (1991) 2493; JP-A 88/68580).

It is an object of the present invention to provide a process which, starting from simple basic chemicals such as alkynes and CO, leads in one step or at most 2 steps to butyrolactones. It is furthermore an object of the present invention to provide butyrolactones substituted in the 3- or 4-position, which are of interest as intermediates in fine product chemistry.

It is finally an object to improve the process for the preparation of 2-(5H)-furanones, from which in a second step butyrolactones can be prepared by hydrogenation, such that industrial preparation is possible.

We have found that this object is achieved by a process for the preparation of butyrolactones of the formula I

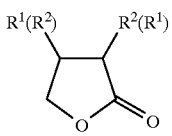

where the substituents $R^1$ and $R^2$ are hydrogen, alkyl or hydroxyalkyl groups preferably having 1 to 8 C atoms or aryl and trialkylsilyl groups, if appropriate carrying inert substituents, by reacting an alkyne of the formula II

$$R^1—C\equiv C—R^2 \qquad II$$

where the substituents have the meanings indicated above, with carbon monoxide and hydrogen gas or with hydrogen formed in situ in the presence of a transition metal catalyst at elevated pressure and elevated temperature. Hydrogen formed in situ is in this case advantageously generated using CO and water by means of the water-gas equilibrium $CO+H_2O \rightleftharpoons H_2+CO_2$.

It was surprising here that it is possible to prepare butyrolactones in one step, ie. that the 2-(5H)-furanones formed as intermediates react further under the reaction conditions to give the butyrolactones.

Alternatively, the preparation, which is known per se, of 2-(5H)-furanones of the formula I

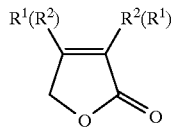

where the substituents $R^1$ and $R^2$ are hydrogen, alkyl or hydroxyalkyl groups, or aryl or trialkylsilyl groups, if appropriate carrying inert substituents, can also be improved by reacting alkynes of the formula II

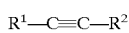

$$R^1—C\equiv C—R^2 \qquad II$$

where $R^1$ and $R^2$ have the abovementioned meanings, with carbon monoxide and hydrogen formed in situ from carbon monoxide and water or with hydrogen gas in the presence of transition metal catalysts, amine bases and halides at 60–140° C. and total pressures of 20–350 bar.

Although Takashi Joh et al. in Organometallics 1991, 10, p. 2494 left column, first paragraph states: "The use of hydrogen gas as a hydrogen source in place of water gave hydroxymethylated product 4 and stilbene 5, and no furanone was obtained", it was surprisingly further found that furanones of the abovementioned formula I are obtained even without the necessity of halide addition if the reaction is carried out at a hydrogen partial pressure of more than 50 bar.

It is then also possible to separately hydrogenate the 2-(5H)-furanones thus obtained in markedly higher spacetime yields in a second step. The hydrogenation can in this case be carried out continuously in a manner known per se or in a batch procedure using hydrogenation catalysts known per se, eg. the catalysts mentioned in Houben-Weyl, Volume 4/2, for the hydrogenation of carbon double bonds. Preferred catalysts are those which contain metals of the VIII subgroup, in particular Rh, Ni or Pd or mixtures of these metals, as active components.

The alkynes of thus formula II can carry identical or different substituents. If the substituents $R^1$ and $R^2$ are different from one another, they can each be incorporated in the reaction product in the 3- or 4-position. In these cases isomer mixtures are thus to be expected. For this reason, in formula I the substituents are depicted alternatively in the 3- or 4-position. The formula thus represents both compounds which carry the substituent $R^1$ in the 3-position and compounds which carry the substituent $R^1$ in the 4-position.

The alkynes II can carry alkyl groups, preferably $C_1$–$C_8$-alkyl groups such as in propyne, 1-butyne, 2-butyne, 1-hexyne and 1-octyne. They can furthermore carry hydroxyalkyl groups, preferably hydroxy-$C_1$–$C_4$-alkyl groups as in 1-butyn-3-ol, 1,4-butynediol and propargyl alcohol. Of the alkynes carrying aryl groups, phenylalkynes are preferred, eg. phenylacetylene and diphenylacetylene. The aryl groups can carry substituents which are stable under the reaction conditions, such as halogen, in particular chlorine, alkoxy, in particular methoxy, and alkyl, in particular $C_1$–$C_4$-alkyl. Furthermore, alkynes are suitable which carry trialkylsilyl groups, eg. trimethylsilylacetylene.

Those alkynes are preferred in which at least one of the substituents $R^1$ and $R^2$ is hydrogen. Acetylene is particularly preferred.

The reaction of the alkyne to give the butyrolactone can be carried out in two technical variants. One embodiment requires the presence of hydrogen gas and is preferred (process A):

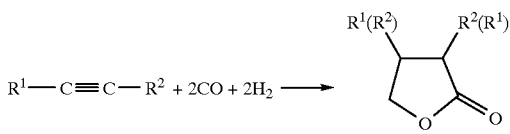

The other variant requires the presence of water (process B):

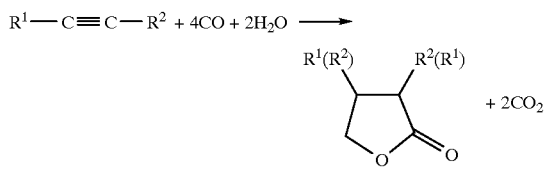

On account of the different overall equation, it is advisable in process A to use at least 2 equivalents, and in process B to use at least 4 equivalents, of CO per equivalent of alkyne. CO can also be employed in excess, where, however, as a rule not more than a 50-fold excess, based on the alkyne, of CO should be used, as even greater excesses convey no discernible technical advantages.

It is also possible to combine variants A and B.

In process A, preferably, from 2 to 50 equivalents of hydrogen $H_2$ are employed per equivalent of alkyne. In a particularly preferred embodiment, the hydrogen is used together with CO in the form of synthesis gas.

In process B, the alkyne of the formula II is reacted with CO and water. Preferably, from 2 to 50 equivalents of water are employed per equivalent of alkyne.

The preparation asccording to the invention of butyrolactones of the formula I is carried out in the presence of transition metal catalysts. In principle, all catalysts can be employed which are able to establish the water-gas equilibrium according to the following equation (water-gas shift catalysts; see Parshall et al., Homogeneous -Catalysis, Wiley, 2nd Edition 1992, Chapter 5.7):

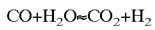

Accordingly, the expression "hydrogen formed in situ" means that the water-gas equilibrium is established and hydrogen is available therefrom.

Both homogeneous and heterogeneous catalysts can be used. Suitable active metal compounds are compounds of rhodium, iridium, ruthenium, osmium, palladium, platinum, iron, nickel, copper and cobalt and also the metals themselves.

Heterogeneous catalysts used can be the metals mentioned or their compounds on inert supports such as carbon, alumina, silica and zirconia. Such catalysts are commercially available or obtainable by known methods, for example by impregnation of inert supports with solutions of the metal compuunds and calcination.

Examples which maye be mentioned are Pd/carbon and Pd/alumina.

The reaction can be carried out in the gas phase, but a liquid-phase reaction is preferred.

Homogeneous catalasts are preferred. The active metals can be employed in the form of halides, acetates, nitrates, oxides, acetylacetonates and, preferably, carbonyls of various valency states, the active compound being formed in the reaction mixture under the reaction conditions.

Ruthenium and nickel compounds are preferred in the process according to the invention, but rhodium compounds are particularly preferred. The latter is surprising, since, according to JA N. 3-94238 (Application Number), for the preparation of the furanones to be postulated as intermediates, ruthenium catalysts should give better yields than rhodium cacatalysts.

By way of example, some transition metal compounds are mentioned below, which are suitable as catalysts according to the invention or precursors of catalysts, from which the catalytically active compound is formed under reaction conditions:

$Rh_6(CO)_{16}$, $Rh_4(CO)_{12}$, $Rh_2O_3$, $RhCl_3.3H_2O$, $RhCl(PPh_3)_3$ (Ph is phenyl), $(codRhCl)_2$ (cod is 1,5-cyclooctadiene), $HRh(CO)(PPh_3)_3$;

$RuCl_3$, $Ru(acac)_3$ (acac is acetylacetonate), $Ru_3(CO)_{12}$, $[CpRu(CO)_2]_2$ (Cp is cyclopentadienyl);

$NiCl_2$, $NiBr_2$, $Ni(CO)_4$, $Ni(cod)_2$, $[Ni(NH_3)_6]Cl_2$;

$PtCl_2$, $PtBr_2$, $PtCl_4$, $PtO_2$, $[Pt(NH_3)_4]Cl_2.H_2O$;

$Pd(ac)_2$ (ac is acetyl), $PdCl_2$, $PdBr_2$, $K_2[PdCl_4]$, $K_2[PdCl_6]$, $Pd(PPh_3)_4$;

$CuCl_2$, $CuBr_2$, $Cu(acac)_2$, $Cu(ac)_2$, $CuO$, $Cu_2O$, $CuI$.

The amount of catalyst employed is generally from 0.01 to 10 mmol per mole of alkyne.

The activity of the transition metal catalysts can be markedly increased by additives. These compounds include amines. Those suitable for this purpose are primary, secondary and tertiary alkylamines and cycloalkylamines as well as nitrogen-containing heterocycles, eg. methylamine, ethylamine, aniline, diethylamine, triethylamine, tributylamine, trioctylamine, pyridine, quinoline, isoquinoline and dimethylaminopyridine. Furthermore, ammonium salts such as triethylammonium hydrochloride, tetraethylammonium chloride, tetrabutylammonium acetate, tetrabutylammonium nitrate and tetrabutylammonium hydroxide show positive effects.

The activity of the catalysts and thus the space-time yields can be considerably increased by addition of halides. Specifically, it is possible to employ alkali metal and alkaline earth metal halides such as NaCl, NaBr, NaI, KCl, KBr, KI, $CaCl_2$, $CaBr_2$ and $CaI_2$ and also halides having organic cations such as tetramethylammonium chloride, tetramethylammonium bromide, tetramethylammonium iodide, tetrabutylammonium chloride, tetrabutylammonium bromide and tetrabutylammonium iodide. Preferred halides are the iodides.

Polymerization inhibitors for olefinically unsaturated organic compounds, such as hydroquinone monomethyl ether, 2,6-di-tert-butyl-4-methylphenol and phenothiazine, are also suitable as additives.

The amount of additives employed is variable within wide limits and can be from 0.1 to 10,000 mol of additive per mole of catalyst. Preferably, from 0.5 to 5 mol per mole of catalyst are employed. One or more additives can be employed in a reaction.

The reaction temperature is in general from 0 to 300° C., preferably 20 to 200° C. and particularly preferably 50 to 150° C. The pressure is generally from 20 to 300 bar. For process A, a pressure from 170 to 280, and for process B from 70 to 280, bar is preferred.

The reaction time is generally from 0.1 to 24 h, preferably 0.5 to 5 h.

The optimum reaction conditions can vary depending on the catalyst selected and on the amount of catalyst employed. It has proven useful in the cases in which larger amounts of the corresponding 2-(5H)-furanone instead of the desired butyrolactone of the formula I are obtained to intensify the reaction conditions, which can be achieved, in particular, by an increase in temperature. A person skilled in the art can easily determine the conditions suitable after a few orientating preliminary tests.

It generally applies that as a rule mixtures of furanones and butyrolactones are formed, mainly furanones being formed under mild reaction conditions and mainly butyrolactones being formed under intensified conditions using catalysts having a strong hydrogenating action. Accordingly, there are no sharp limits to furanone and butyrolactone formation. If, for example, halide is additionally used, mainly butyrolactones are formed with high space-time yields; in process A even at mild temperatures of about 80–100° C.

Accordingly, it may be useful to prepare only mixtures containing mainly butyrolactone. The mixtures can then be subjected to hydrogenation either directly or separated into their individual components, butyrolactone and furanone. The furanone can be fed back into the reaction or separately hydrogenated.

The reaction can be carried out in the gas phase and preferably in the liquid phase. In the liquid phase, organic solvents which are inert under the reaction conditions can be added, for example alkanols such as methanol, ethanol and isopropanol, ethers such as diethyl ether, methyl tert-butyl ether, tetrahydrofuran and 1,4-dioxane, ketones such as acetone, esters such as methyl acetate and ethyl acetate, furthermore aromatic hydrocarbons such as benzene and toluene, aliphatic hydrocarbons such as pentane and hexane and also polar, aprotic solvents such as N-methylpyrrolidone. The amounts can be from 5 to 95% by weight of solvent, based on the reaction mixture.

The process according to the invention can be carried out continuously or batchwise in pressure-tight reactors such as stirred, tubular or loop reactors.

In the batchwise procedure, the alkyne of the formula II, the catalyst and, if appropriate, a solvent and additives can be initially introduced into the reactor. In reactions with acetylene the corresponding acetylene pressure is set. In process B, the required amount of water can furthermore be added to the reaction mixture. The reaction pressure can then be set using CO. Then in process A hydrogen is added up to the desired pressure, if synthesis gas is not employed from the start. After completion of the reaction the pressure is released, it being possible to use released gases for subsequent reactions. The working-up of the reaction products is carried out by known methods, preferably by distillation. Solvents, catalyst and additives can likewise be reused in further reactions after working-up thereof.

In a preferred continuous embodiment, in the reaction of acetylene the latter can be dissolved in a solvent in a saturator. The catalyst and, if appropriate, water and additives are also dissolved. This solution is compressed to the reaction pressure and pumped into the reactor. CO, further acetylene and, if appropriate, hydrogen are introduced into the reactor via a gas jet. The pressure of the reaction product is released, the liquid phase is worked up by distillation and the catalyst is fed back into the reaction cycle. The gas phase, if appropriate after a purification step, can also be fed back into the reactor.

EXAMPLES

Example 1 (process A)

30 mg (0.028 mmol) of $Rh_6(CO)_{16}$ and 0.66 g (6.6 mmol) of triethylamine were initially introduced into 135 ml of dioxane. 39.1 mmol of acetylene were injected, a pressure of 3.4 bar being established. The pressure was then increased to 100 bar using carbon monoxide and to 200 bar using hydrogen. The mixture was stirred at 120° C. for 5 h. After releasing the pressure of the reactor and working up by distillation, butyrolactone was isolated in 82% yield.

Example 2 (process A)

The reaction was carried out similarly to Example 1, but at 80° C. The yield of butyrolactone was 67%.

Example 3 (process A)

30 mg (0.028 mmol) of $Rh_6(CO)_{16}$, 0.66 g (6.6 mmol) of triethylamine, 40 mg (0.32 mmol) of hydroquinone monomethyl ether and 12.5 mg (0.08 mmol) of NaI were initially introduced into 65 ml of dioxane. 39.1 mmol of acetylene were injected, a pressure of 3.4 bar being established. The pressure was then increased to 100 bar using carbon monoxide and to 200 bar using hydrogen. The mixture was stirred at 100° C. for 1.5 h. After releasing the pressure of the reactor and working up by distillation, butyrolactone was isolated in 84% yield.

Example 4 (process B)

30 mg (0.028 mmol) of $Rh_6(CO)_{16}$, 0.66 g (6.6 mmol) of triethylamine, 4.48 g of water, 40 mg (0.32 mmol) of hydroquinone monomethyl ether and 12.5 g (0.08 mmol) of NaI were initially introduced into 65 ml of dioxane. 39.5 mmol of acetylene were injected, a pressure of 3.5 bar being established. The pressure was increased to 200 bar using carbon monoxide. The mixture was stirred at 150° C. for 1.5 h. After releasing the pressure of the reactor and working up by distillation, butyrolactone was isolated in 71% yield.

Example 5 (process B)

30 mg (0.028 mmol) of $Rh_6(CO)_{16}$, 0.66 g (6.6 mmol) of triethylamine, 4.48 g (249 mmol) of water, 40 mg (0.36 mmol) of hydroquinone monomethyl ether and 12.5 mg (0.08 mmol) of NaI were initially introduced into 65 ml of dioxane. 56.6 mmol of acetylene were injected, a pressure of 5.9 bar being established. The pressure was then increased to 100 bar using carbon monoxide. The mixture was stirred at 80° C. for 2 h. After releasing the pressure of the reactor and working up by distillation, 2-(5H)-furanone was isolated in 84% yield.

Example 6 (process B)

30 mg (0.028 mmol) of $Rh_6(CO)_{16}$, 0.66 g (6.6 mmol) of triethylamine, 4.48 g (249 mmol) of water, 21 mg (0.169 mmol) of 2,4,6-trimethylpyridine and 12.5 mg (0.08 mmol) of NaI were initially introduced into 65 ml of dioxane. 57 mmol of acetylene were injected, a pressure of 6.0 bar being established. The pressure was then increased to 100 bar using carbon monoxide. The mixture was stirred at 80° C. for 2 h. After releasing the pressure of the reactor and working up by distillation, 2-(5H)-furanone was isolated in 85% yield.

Example 7 (process A)

30 mg (0.028 mmol) of $Rh_6(CO)_{16}$, 0.66 g (6.6 mmol) of triethylamine and 12.5 mg (0.08 mmol) of NaI were initially introduced into 65 ml of dioxane. 57 mmol of acetylene were injected, a pressure of 5.8 bar being established. The pressure was increased to 80 bar using carbon monoxide and then to 200 bar using hydrogen. The mixture was stirred at 100° C. for 1 h. After releasing the pressure of the reactor and working up by distillation, 2-(5H)-furanone was isolated in 67% yield.

Example 8 (hydrogenation of 2-(5H)-furanone)

5.0 g of the 2-(5H)-furanone prepared by the process according to the invention and freed of catalyst together with 100 ml of dioxane and 0.5 g of a hydrogenation catalyst (5% weight Pd on carbon) were initially introduced into a 250 ml stirred flask, which was equipped with an aerating stirrer and a gas burette.

The solution was aerated with hydrogen at room temperature and normal pressure. After 30 min, the absorption of hydrogen was complete. After removal of catalyst and solvent, γ-butyrolactone was isolated in a yield of 96%.

We claim:

1. A process for the preparation of butyrolactones of the formula I

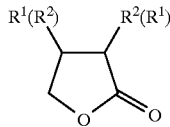

I where the substituents $R^1$ and $R^2$ are hydrogen, alkyl or hydroxyalkyl groups, or aryl and trialkylsilyl groups, if appropriate carrying inert substituents, which comprises reacting an alkyne of the formula II

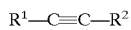

II where the substituents have the meanings indicated above, with carbon monoxide and hydrogen gas or with hydrogen formed in situ in the presence of a transition metal catalyst at elevated pressure and elevated temperature.

2. A process as claimed in claim 1, wherein the hydrogen formed in situ is generated by means of the water-gas equilibrium using CO and water.

3. A process as claimed in claim 1, wherein the reaction is carried out in the presence of an amine or of an ammonium salt.

4. A process as claimed in claim 1, wherein rhodium or ruthenium compounds are used as catalyst.

5. A process as claimed in claim 1, wherein a rhodium carbonyl compound is used as transition metal catalyst.

6. A process as claimed in claim 1, wherein acetylene is used as alkyne of the formula II.

7. A process as claimed in claim 1, wherein at least 2 equivalents of CO and 2 equivalents of hydrogen $H_2$ are used per equivalent of alkyne of the formula II at a reaction pressure of from 170 to 280 bar.

8. A process as claimed in claim 1, wherein at least 4 equivalents of CO and 2 equivalents of water are used per equivalent of alkyne of the formula II at a reaction pressure of from 70 to 280 bar.

9. A process as claimed in claim 1, wherein the reaction is carried out in the presence of a halide.

10. A process as claimed in claim 1, wherein the reaction is carried out in the presence of an iodide.

11. A process as claimed in claim 1, wherein the reaction is carried out in the presence of a polymerization inhibitor.

12. A process for the preparation of 2-(5H)-furanones of the formula I

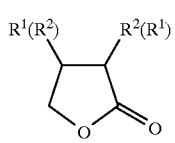

I where the subcstituents $R^1$ and $R^2$ are hydrogen, alkyl or hydroxyalkyl groups, or aryl or trialkylsilyl groups, if appropriate carrying inert substituents, which comprises reacting alkynes of the formula II

II where $R^1$ and $R^2$ have the abovementioned meanings, with carbon monoxide and hydrogen gas in the presence of transition metal catalysts and amine bases at 60–140° C. and a hydrogen partial pressure of more than 50 bar.

13. A process as claimed in claim 1, wherein 2-(5H)-furanones of the formula I.

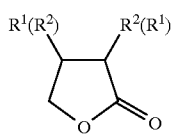

I where $R^1$ and $R^2$ have the meanings indicated in claim 10, are first prepared by the process as claimed in claim 12 and these are hydrogenated to the corresponding butyrolactones in a separate hydrogenation reaction.

14. A process as claimed in claim 13, wherein acetylene is used as a starting material and butyrolactone is prepared.

* * * * *